(12) United States Patent
Hallberg et al.

(10) Patent No.: US 9,370,336 B2
(45) Date of Patent: Jun. 21, 2016

(54) MODEL-BASED METHOD FOR ASSESSING ACOUSTIC SIGNAL QUALITY IN HEART MONITORING DEVICE

(71) Applicant: Sharp Laboratories of America, Inc., Camas, WA (US)

(72) Inventors: Bryan Severt Hallberg, Vancouver, WA (US); Fredrick Norman Hill, Portland, OR (US)

(73) Assignee: Sharp Laboratories of America, Inc., Camas, WA (US)

( * ) Notice: Subject to any disclaimer, the term of this patent is extended or adjusted under 35 U.S.C. 154(b) by 445 days.

(21) Appl. No.: 13/894,528

(22) Filed: May 15, 2013

(65) Prior Publication Data

US 2014/0343446 A1 Nov. 20, 2014

(51) Int. Cl.
*A61B 7/04* (2006.01)
(52) U.S. Cl.
CPC ........................................ *A61B 7/04* (2013.01)
(58) Field of Classification Search
CPC ........................................................ A61B 7/04
USPC .......................................................... 600/528
See application file for complete search history.

(56) References Cited

U.S. PATENT DOCUMENTS

| 4,436,096 | A | | 3/1984 | Dyck et al. |
| 4,781,200 | A | | 11/1988 | Baker |
| 4,862,361 | A | | 8/1989 | Gordon et al. |
| 5,047,930 | A | | 9/1991 | Martens et al. |
| 5,533,511 | A | * | 7/1996 | Kaspari .............. A61B 5/02007 |
| | | | | 128/925 |
| 6,210,344 | B1 | | 4/2001 | Perin et al. |
| 6,805,671 | B2 | | 10/2004 | Stergiopoulos et al. |
| 7,532,923 | B1 | | 5/2009 | Hayes-Gill et al. |
| 7,689,271 | B1 | | 3/2010 | Sullivan |
| 2008/0228095 | A1 | | 9/2008 | Richardson |
| 2008/0234594 | A1 | * | 9/2008 | Brooks ................ A61B 5/0402 |
| | | | | 600/513 |

* cited by examiner

*Primary Examiner* — Christopher D Koharski
*Assistant Examiner* — Jeremiah Kimball
(74) *Attorney, Agent, or Firm* — Scot A. Reader

(57) ABSTRACT

A model-based method for assessing acoustic signal quality in a heart monitoring device. The personal heart sound interval distribution of a person being actively monitored is compared with a modeled global heart sound interval distribution shared by most human beings after which processing action is taken consistent with the quality assessment. The error in the best fit between the personal interval distribution and the global interval distribution is presumed to be caused predominantly by noise, allowing the quality of the fit to serve as a proxy for the level of noise in the acoustic signal and used in making processing decisions.

12 Claims, 4 Drawing Sheets

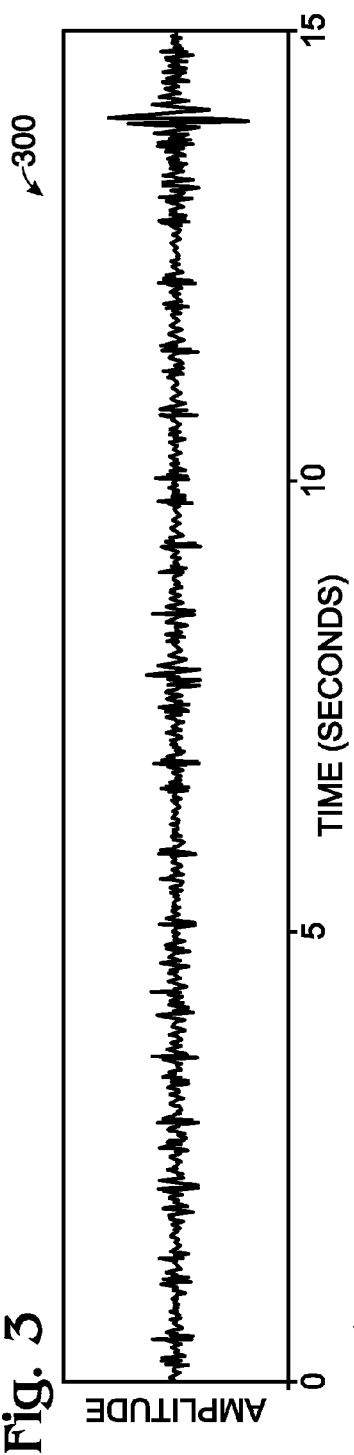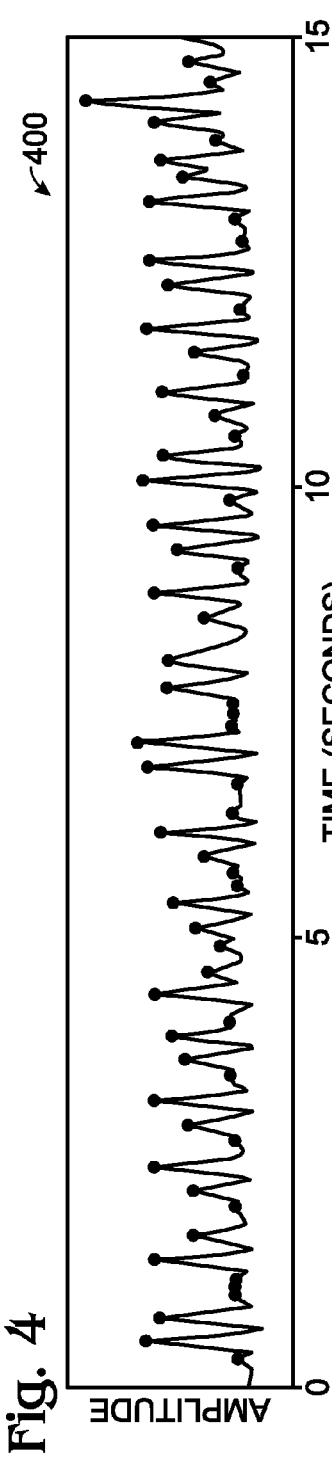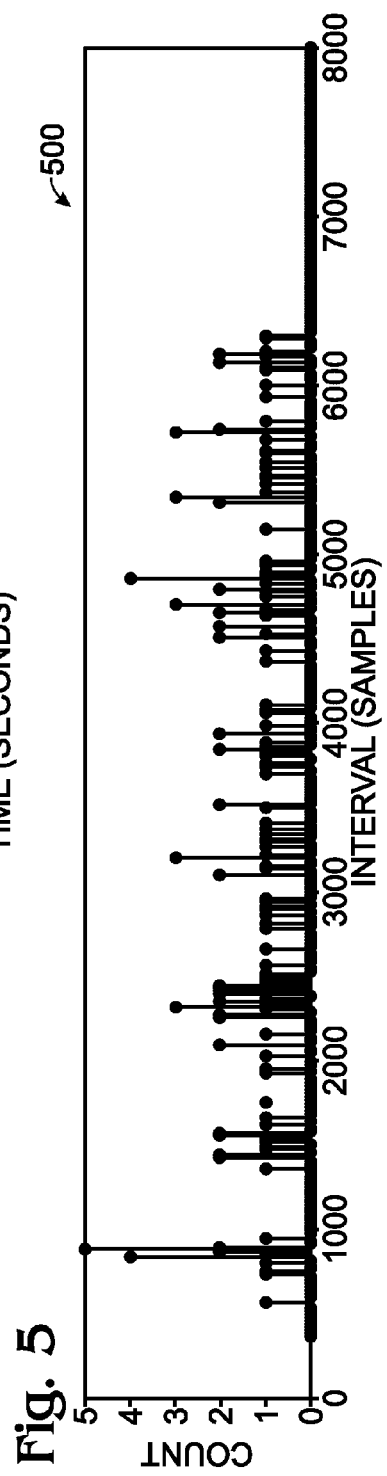

MODEL-BASED METHOD FOR ASSESSING ACOUSTIC SIGNAL QUALITY IN HEART MONITORING DEVICE

BACKGROUND OF THE INVENTION

The present invention relates to physiological monitoring and, more particularly, to mobile heart monitoring.

Mobile heart monitoring can be helpful in saving lives and maintaining the health of people as they go about their daily lives. For example, a mobile heart monitoring device can promptly discover and notify a person wearing the device of a heart malady so that the person can seek emergency medical treatment or take other appropriate health-preserving action.

Mobile heart monitoring often invokes the body sound method, which is sometimes called auscultation. In the body sound method, an acoustic transducer mounted on the body of the person generates an acoustic signal capturing heart sounds. A pulse sequence is then identified in the acoustic signal and parameters indicative of heart function, such as heart rate, are estimated from the pulse sequence. The heart parameter estimates are then provided locally on an ambulatory heart monitoring device and/or remotely to a clinician.

One problem commonly encountered in mobile acoustic heart monitoring is parameter estimation error caused by noise. An acoustic signal that contains body sounds can be disrupted by several types of noise, including long-term, moderate amplitude noise introduced by the surrounding environment and short-term, high amplitude noise introduced by impulse events such as talking, coughing or sneezing. Regardless of the source, noise can mask heart sounds, which can result in inability to recover the pulse sequence or provision of erroneous heart parameter estimates. Either of these noise-induced problems can have serious adverse consequences on the health of the person being monitored. Inability to recover the pulse sequence can prevent a person being monitored or his or her clinician from promptly discovering a heart problem and taking appropriate action, whereas provision of erroneous heart parameter estimates can lead the person or clinician to make an incorrect diagnosis and cause the person to undergo treatment that is not medically indicated or forego treatment that is medically indicated.

SUMMARY OF THE INVENTION

The present invention provides a model-based method for assessing acoustic signal quality in a heart monitoring device. In the invention, the personal heart sound interval distribution of a person being actively monitored is compared with a modeled global heart sound interval distribution shared by most human beings, after which processing action is taken consistent with the quality assessment. The invention makes use of the fact that human heart sound has two fundamental components, often called the S1 and S2 sounds, having common interval characteristics across a broad swath of humanity. The S1 sound is caused by turbulence during the closure of the mitral and tricuspid valves and marks the start of systole. The S2 sound is caused by the closure of the aortic and pulmonic valves and marks the end of systole. As such, the S1 and S2 sounds alternate. Moreover, when most people are at rest, or are only moderately active, the interval between an S1 sound and the next S2 sound is less than the interval between an S2 sound and the next S1 sound. These widely shared attributes of human heart sound enable definition of a global heart sound interval distribution that, with minor adjustments to interval ratios to account for small differences between subjects and activity levels, will usually fit closely with the personal heart sound interval distribution of a person being monitored in the absence of noise. Accordingly, the quality of the best fit between the personal interval distribution and the ratio-adjusted global interval distribution usually serves as a close proxy for the level of noise in the acoustic signal and can be used in making processing decisions, such as whether or not to output a heart parameter estimate using the signal segment exhibiting the noise, whether or not (and if so how) to update a configurable signal processing element (e.g., filter cutoff frequency, amplitude threshold, etc.) to reduce noise in subsequent signal segments, and in generating a confidence indicator for a heart parameter estimate computed using the signal segment exhibiting the noise.

In one aspect of the invention, a heart monitoring device comprises: a sound capture element configured to generate an acoustic signal capturing heart sounds; and an acoustic signal processing element operatively coupled with the capture element and configured to generate from the acoustic signal over a time window a personal heart sound interval distribution, determine a best fit between the personal interval distribution and a global heart sound interval distribution, determine a fit quality value indicative of quality of the best fit and select a processing action for the time window using the fit quality value.

In some embodiments, the processing element is configured to determine the best fit at least in part by generating a personal heart sound interval distribution curve and comparing fit errors between the personal interval distribution curve and a parameterized global heart sound interval distribution curve for different values of at least one parameter of the global interval distribution curve.

In some embodiments, the processing action comprises reconfiguring a signal processing element for application to the acoustic signal over a future time window.

In some embodiments, the processing action comprises generating a heart parameter estimate for the time window.

In some embodiments, the processing action comprises generating a confidence indicator for the time window.

In some embodiments, the processing action comprises inhibiting determination of a heart parameter estimate for the time window.

In some embodiments, the processing element is further configured to compare the fit quality value with a quality threshold and, based on the comparison, select the processing action.

In some embodiments, the processing action comprises determining a heart parameter estimate and confidence indicator for the time window, and the device further comprises a heart data output element operatively coupled with the processing element and configured to display the heart parameter estimate and the confidence indicator.

In some embodiments, the processing element is configured to generate the personal interval distribution at least in part by detecting an envelope of the acoustic signal over the time window.

In some embodiments, the processing element is further configured to generate the personal interval distribution at least in part by generating a histogram including counts of intervals between peaks in the envelope for intervals of different durations.

In some embodiments, the processing element is further configured to generate the personal interval distribution at least in part by smoothing the histogram to generate a personal heart sound interval distribution curve.

In some embodiments, the device is a mobile device.

In another aspect of the invention, a model-based method for assessing acoustic signal quality in a heart monitoring device comprises: generating by the device an acoustic signal capturing heart sounds; generating by the device from the acoustic signal over a time window a personal heart sound interval distribution; determining by the device a best fit between the personal interval distribution and a global heart sound interval distribution; determining by the device a fit quality value indicative of quality of the best fit; and selecting by the device a processing action for the time window using the fit quality value.

These and other aspects of the invention will be better understood by reference to the following detailed description taken in conjunction with the drawings that are briefly described below. Of course, the invention is defined by the appended claims.

BRIEF DESCRIPTION OF THE DRAWINGS

FIG. 3 is a plot showing an acoustic signal over a time window.

FIG. 4 is a plot showing an envelope of the acoustic signal over the time window.

FIG. 5 is a plot showing a histogram of counts of intervals between peaks in the envelope for intervals of different durations.

DETAILED DESCRIPTION OF A PREFERRED EMBODIMENT

As a preliminary matter, it bears noting that the intervals between adjacent S1 and S2 heart sounds fall into four basic classes:

S12: The interval between an S1 sound and the next S2 sound.

S21: The interval between an S2 sound and the next S1 sound.

S11: The interval between an S1 sound and the next S1 sound.

S22: The interval between an S2 sound and the next S2 sound.

In the description that follows, intervals that span more than a single heartbeat are denoted with prime notation. For example S12' indicates the interval between an S1 sound and the second following S2 sound.

Figure 1:
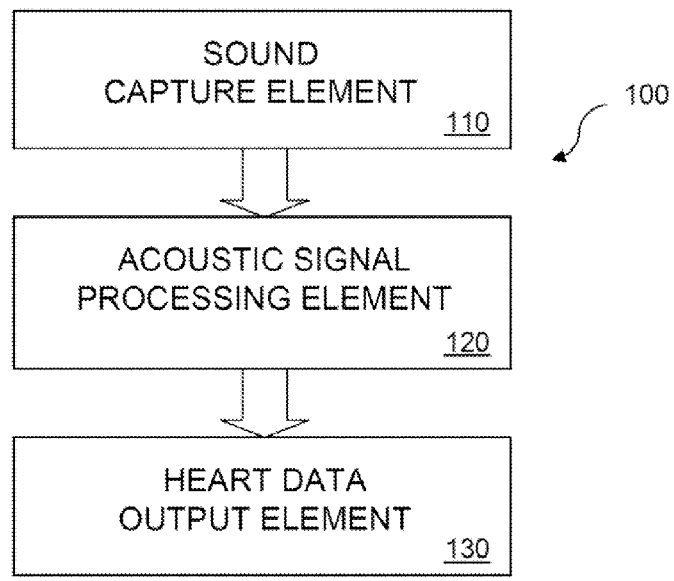
FIG. 1 is a block diagram of a mobile heart monitoring device.

Turning now to FIG. 1 a heart monitoring device 100 is shown in some embodiments of the invention. Monitoring device 100 includes a sound capture element 110, an acoustic signal processing element 120 and a heart data output element 130, which are communicatively coupled in series.

Capture element 110 includes a sound transducer that continually detects S1 and S2 heart sounds at a detection point, such as the trachea, chest or back of a person being monitored and continually transmits an acoustic signal containing the detected heart sounds to processing element 120. The S1 heart sound is caused by turbulence during the closure of the mitral and tricuspid valves of the person being monitored and marks the start of systole. The S2 heart sound is caused by the closure of the aortic and pulmonic valves of the person being monitored and marks the end of systole. Capture element 110 may include a microphone to detect heart sounds and signal acquisition elements, such as an amplifier, filter and analog/digital (A/D) converter, to help transform detected heart sounds into the acoustic signal containing detected heart sounds.

Processing element 120 continually receives the acoustic signal from capture element 110 and uses the acoustic signal to estimate one or more heart parameters for the person being monitored, including heart rate, during discrete time windows. Processing element 120 also generates confidence indicators for heart parameter estimates for discrete time windows. Processing element 120 transmits the heart parameter estimates and the confidence indicators to output element 130.

Output element 130 has a display screen for displaying heart parameter estimates and confidence indicators received from processing element 120. In some embodiments, output element 130, in addition to a display screen, has an interface to an internal or external data management system that stores heart parameter estimates and confidence indicators received from processing element 120 and/or an interface that transmits such information to a remote monitoring device, such as a monitoring device at a clinician facility. Information displayed on output element 130 may also include information derived from heart parameter estimates and confidence indicators, such as color-coded indicators of present heart health.

In some embodiments, capture element 110, processing element 120 and output element 130 are part of a mobile heart monitoring device that monitors a person's heart health in real-time as the person goes about daily activities.

Figure 2:
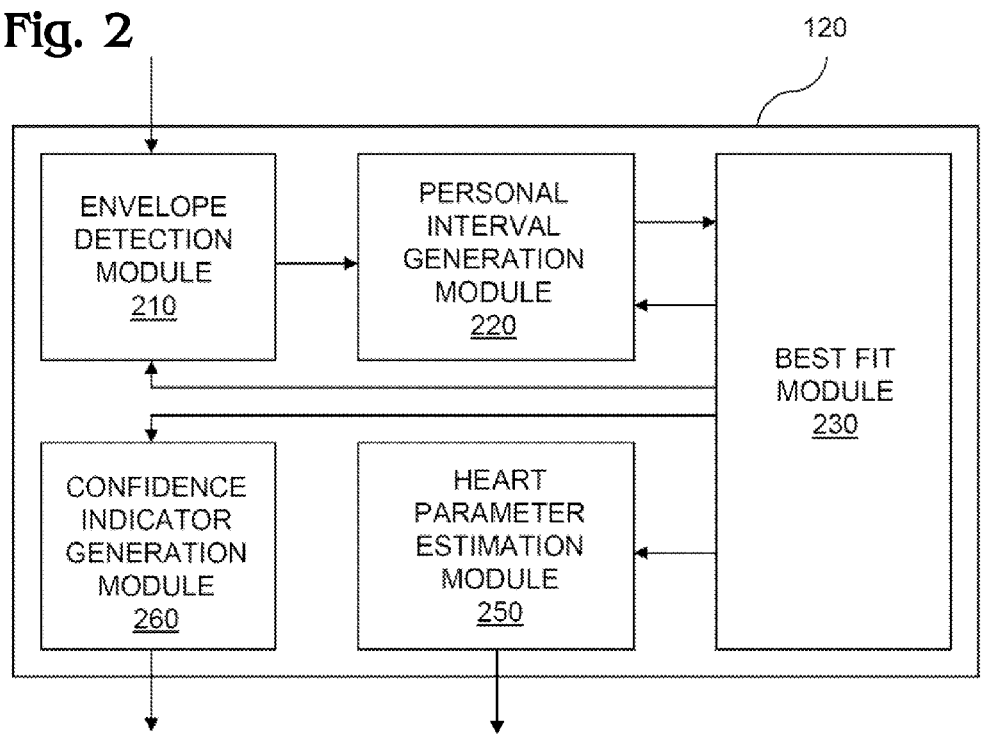
FIG. 2 is a block diagram of an acoustic signal processing element.

FIG. 2 shows processing element 120 in more detail. Processing element 120 receives as continual input an acoustic signal from capture element 110 and processes the acoustic signal as a series of signal segments of a predetermined duration, such as fifteen seconds. Signal segments may or may not overlap. The predetermined duration is generally selected to be between ten and thirty seconds to maintain accuracy and minimize statistical drift. Each signal segment contains a time sequence of digital samples having various amplitudes that represent detected heart sounds and noise at different times within the predetermined time window. FIG. 3 shows an exemplary fifteen second signal segment 300 received from capture element 110.

Each signal segment is processed by an envelope detection module 210, which filters, rectifies and smoothes the signal segment to generate a signal envelope which clearly expresses times of S1 and S2 heart sounds as signal peaks over the time window covered by the signal segment. Purely by way of example, envelope detection module 210 may apply to each signal segment a digital band-pass filter, followed by an absolute value converter, followed by a digital low-pass filter. Continuing with the previous example, FIG. 4 shows a signal envelope 400 generated from signal segment 300 with signal peaks marked with a bold dot notation.

Each signal envelope is then processed by a personal interval generation module 220, which computes a personal heart sound interval distribution curve for the person being monitored over the time window covered by the signal segment. Module 220 identifies peaks in the signal envelope and computes intervals between peaks. Module 220 then generates a histogram by tallying the number of occurrences of intervals of different durations. Continuing with the above example, FIG. 5 shows a histogram 500 of counts of intervals between peaks in signal envelope 400 for intervals of different durations. Each interval in histogram 500 spans a sample range which is readily convertible to a time range (e.g., seconds) based on the operative sampling rate.

Figure 6:
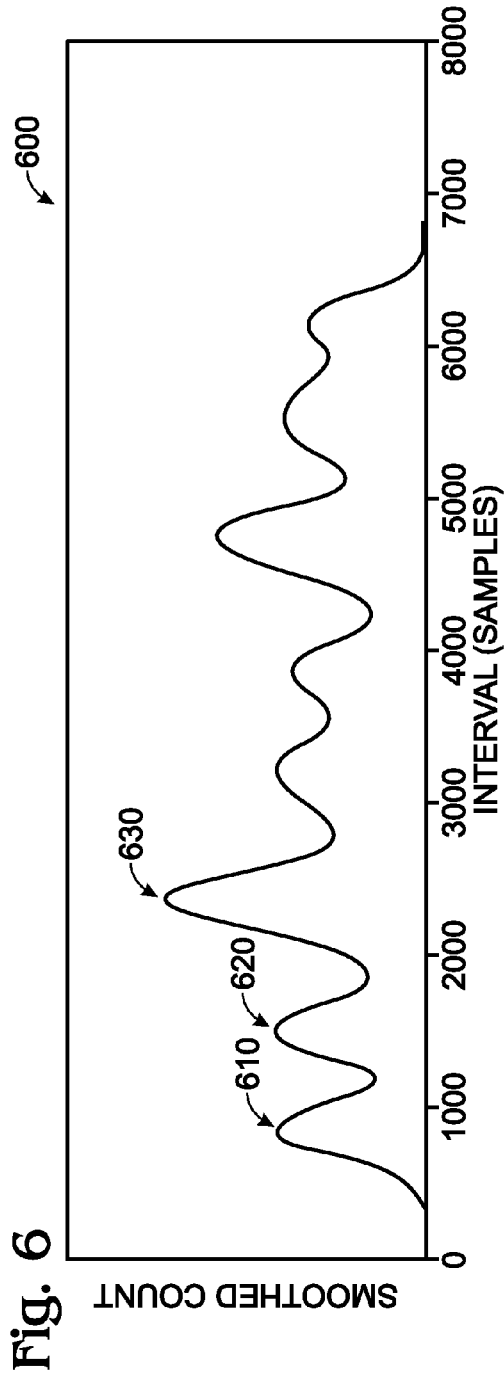
FIG. 6 is a plot showing a personal heart sound interval distribution curve over the time window.

After generating the histogram, module 220 smoothes the histogram to generate the personal interval distribution curve. Smoothing may be accomplished by applying a low-pass filter to the histogram. Continuing with the above example, FIG. 6 shows a personal heart sound interval distribution curve 600 generated by smoothing of histogram 500. The y-axis is a smoothed count, which approximates the probability density of heart sound intervals for the person being monitored over the time window covered by signal segment 300. The x-axis is expressed in samples and is readily convertible to seconds via the operative sampling rate. Peaks 610, 620, 630 are clearly expressed in the smoothed count at x-axis locations where intervals were concentrated in histogram 500.

Each personal interval distribution curve is then processed by a best fit module 230, which compares the personal interval distribution curve with a parameterized global heart sound interval distribution curve configured within a memory element on module 230 to assess signal quality over the time window covered by the signal segment and select processing actions consistent with the quality assessment. As discussed earlier, the fundamental S1 and S2 heart sounds have common interval characteristics across most of humanity which enables modeling of a global heart sound interval distribution that, with minor adjustments to interval ratios to account for variability between subjects and activity levels, will usually fit closely with the personal heart sound interval distribution of a person being monitored in the absence of noise. Thus, the quality of the best fit between the personal interval distribution and the ratio-adjusted global interval distribution can be presumed to be caused predominantly by noise, which allows the fit error to serve as a proxy for the level of noise in the acoustic signal and used in making processing decisions, such as whether or not to output a heart parameter estimate using the signal segment exhibiting the noise, whether or not (and if so how) to update a configurable signal processing element (e.g., filter cutoff frequency, amplitude threshold, etc.) to reduce noise in subsequent signal segments, and in generating a confidence indicator for a heart parameter estimate computed using the signal segment exhibiting the noise.

Figure 7:
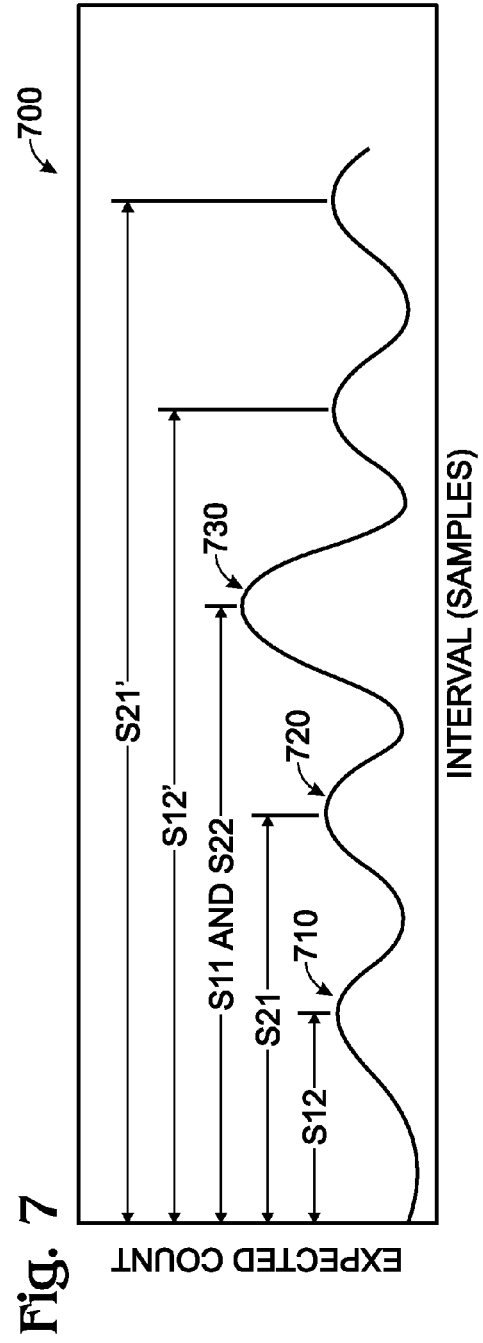
FIG. 7 is a plot showing a global heart sound interval distribution curve.

The global interval distribution curve may be modeled from empirical data. For most healthy human subjects at rest, the interval between an S1 sound and the next S2 sound (S12) is roughly one-third of the interval between consecutive S1 sounds (S11); the interval between an S2 sound and the next S1 sound (S21) is roughly two-thirds of the interval between consecutive S1 sounds (S11); and the interval between consecutive S1 sounds (S11) is roughly equal to the interval between consecutive S2 sounds (S22). Applying these observed attributes of human heart sound in a Gaussian random process using a standard deviation substantially less than the mean S11 interval yields a global heart sound interval distribution curve 700 illustrated in FIG. 7 having a first lobe 710 with a peak at the median S12 interval, a second lobe 720 with a peak at the median S21 interval and a third lobe 730 twice the height of lobes 710, 720 with a peak at the shared median S11 and S22 intervals. Additional lobes corresponding to heart sound intervals traversing multiple heart cycles (S12', S21') are shown on curve 700 and marked with prime notation.

Parameters of the global interval distribution curve are determined by the best fit with the personal interval distribution curve within a range that may be determined by a parameter history. As such, the value of the parameters will vary over time within a defined range of values to provide sufficient degrees of freedom in the global interval distribution curve to capture (with low fit error) variation in human heart sound interval distribution attributable to human differences and present activity level. The global interval distribution curve thus yields a slightly different curve for different values of its parameters. As such, the global interval distribution curve might be viewed as a family of curves associated with different parametric values. Two examples of parameters of the global interval distribution curve that model variability in human heart sound interval distribution are mean S11 interval and gamma, which represents the ratio of the mean S12 interval and the mean S11 interval.

Figure 8:
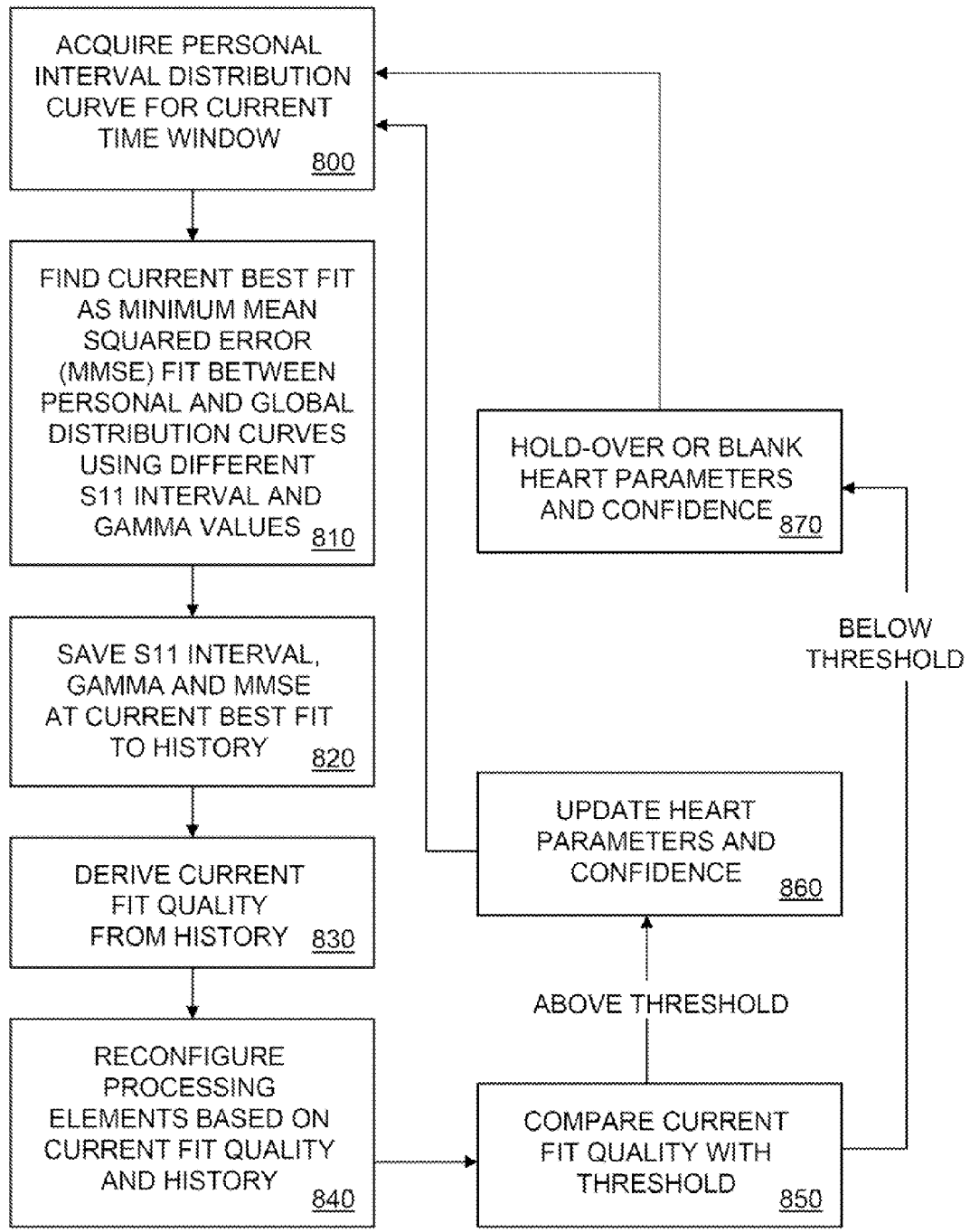
FIG. 8 is a flow diagram showing steps of a model-based method for assessing acoustic signal quality performed by an acoustic signal processing element.

Turning now to FIG. 8, steps of a model-based method for assessing acoustic signal quality are shown. These steps are performed by best fit module 230. At the outset, module 230 acquires a personal heart sound interval distribution curve for a first signal segment (800). Continuing the above example, the personal distribution curve will generally look similar to curve 600, wherein peaks 610, 620 representing the S12 and S21 interval distributions, respectively, are followed by a peak 630 of roughly twice the smoothed count representing the combined S11 and S22 interval distributions.

Next, module 230 determines a current best fit between the personal interval distribution curve and the parameterized global interval distribution curve using different values of different parameters, including mean S11 interval and gamma, which represents the ratio of the mean S12 interval and the mean S11 interval (810). In this regard, while shared characteristics of the human heart sound enable definition of a global interval distribution curve that normally fits very well with the personal interval distribution curve of a person being monitored, minor adjustments to heart sound interval ratios in the global interval distribution curve can reduce fit error attributable to variability between subjects and activity levels. Thus, module 230 compares the personal interval distribution curve and the global interval distribution curve for different values of mean S11 interval and gamma and selects as the best fit the comparison which exhibits the minimum mean squared error (MMSE).

Next, module 230 saves to a history within a memory element on module 230 current best fit results from the most recent best fit determination. The saved results include, for example, values of mean S11 interval, gamma and MMSE at the best fit (820). The applicable time is saved along with the results. The history includes a predetermined number of best fit results from the immediate past, which may age-out of the memory element in FIFO order.

Next, module 230 derives a current fit quality value from the history (830). The fit quality value may be determined using the values of mean S11 interval, gamma and MMSE within the current best fit results and the values of mean S11 interval, gamma and MMSE within best fit results from the immediate past. Invoking values from past best fit results can help mitigate parameter estimation error.

Next, module 230 selects one or more processing actions based on the current fit quality value and the history (840). For example, module 230 may prompt envelope detection module 210 to reconfigure a signal processing element (e.g., change a filter cutoff frequency, change an amplitude threshold, etc.) to reduce noise in subsequent signal segments. Naturally, additional or different processing actions may be selected depending on the current fit quality value and the history.

Next, module 230 compares the current fit quality value with a predetermined quality threshold (850). In this regard, if the fit error of the current best fit is not excessive, it is presumed that the current signal does not have an excessive noise component and is reliable. On the other hand, if the fit error of the current best fit is excessive (i.e., low-quality best fit), it is presumed that the current signal segment has an excessive noise component and is unreliable.

If module 230 determines that the current fit quality value is above the quality threshold, module 230 prompts heart parameter estimation module 250 to compute a heart parameter estimate for the current signal segment (e.g., heart rate estimate) for output and display on output element 130 and prompts confidence indicator generation module 260 to generate a confidence indicator for the current signal segment for output and display on output element 130 (850). Naturally, additional or different processing actions may be selected.

On the other hand, if module 230 determines that the current fit quality value is below the quality threshold, module 230 causes the heart rate estimate and confidence indicator outputted and/or displayed by output element 130 to be held-over from the previous signal segment or blanked (e.g., by outputting and/or displaying an unavailability indication) (870).

In either event, module 230 then proceeds to receive from module 220 and process the personal interval distribution curve for the next signal segment (800).

In some embodiments, operations described as being performed by modules 210-260 are implemented by a microprocessor executing software instructions. In these embodiments, arrows between modules 210-260 may represent an algorithmic processing sequence that does not necessarily involve transmission of data between modules 210-260 over physical lines. In other embodiments, operations described as being performed by one or more of modules 210-260 may be implemented by a microcontroller executing firmware or in custom logic (e.g., an application specific integrated circuit).

It will be appreciated by those of ordinary skill in the art that the invention can be embodied in other specific forms without departing from the spirit or essential character hereof. The present description is considered in all respects to be illustrative and not restrictive. The scope of the invention is indicated by the appended claims, and all changes that come within the meaning and range of equivalents thereof are intended to be embraced therein.

What is claimed is:

1. A heart monitoring device, comprising:
   a sound capture element configured to capture heart sounds and generate an acoustic signal containing the heart sounds; and
   an acoustic signal processing element operatively coupled with the capture element and configured to generate from the acoustic signal over a time window a personal heart sound interval distribution, determine a best fit between the personal interval distribution and a global heart sound interval distribution, determine a fit quality value indicative of quality of the best fit and select a processing action for the time window using the fit quality value, wherein the processing element is configured to determine the best fit at least in part by generating a personal heart sound interval distribution curve and comparing fit errors between the personal interval distribution curve and a parameterized global heart sound interval distribution curve for different values of at least one parameter of the global interval distribution curve.

2. The device of claim 1, wherein the processing action comprises reconfiguring a signal processing element for application to the acoustic signal over a future time window.

3. The device of claim 1, wherein the processing action comprises generating a heart parameter estimate for the time window.

4. The device of claim 1, wherein the processing action comprises generating a confidence indicator for the time window.

5. The device of claim 1, wherein the processing action comprises inhibiting determination of a heart parameter estimate for the time window.

6. The device of claim 1, wherein the processing element is further configured to compare the fit quality value with a quality threshold and, based on the comparison, select the processing action.

7. The device of claim 1, wherein the processing action comprises determining a heart parameter estimate and confidence indicator for the time window, further comprising a heart data output element operatively coupled with the processing element and configured to display the heart parameter estimate and the confidence indicator.

8. The device of claim 1, wherein the processing element is configured to generate the personal interval distribution at least in part by detecting an envelope of the acoustic signal over the time window.

9. The device of claim 8, wherein the processing element is further configured to generate the personal interval distribution at least in part by generating a histogram including counts of intervals between peaks in the envelope for intervals of different durations.

10. The device of claim 9, wherein the processing element is further configured to generate the personal interval distribution at least in part by smoothing the histogram to generate the personal heart sound interval distribution curve.

11. The device of claim 1, wherein the device is a mobile device.

12. The device of claim 3, further comprising a heart data output element operatively coupled with the processing element and configured to display the heart parameter estimate.

* * * * *